United States Patent
Kitron et al.

(10) Patent No.: US 8,530,435 B2
(45) Date of Patent: Sep. 10, 2013

(54) BRASSINOSTEROIDS IN TREATING PROSTATIC HYPERPLASIA AND ANDROGENIC ALOPECIA

(75) Inventors: Amir Kitron, Tene (IL); Rochel Pergamentz, Tene (IL)

(73) Assignee: Grasses of Eden Ltd., Moshav Carmel, IL (US)

( * ) Notice: Subject to any disclaimer, the term of this patent is extended or adjusted under 35 U.S.C. 154(b) by 65 days.

(21) Appl. No.: 13/151,415

(22) Filed: Jun. 2, 2011

(65) Prior Publication Data

US 2011/0319348 A1 Dec. 29, 2011

Related U.S. Application Data

(63) Continuation-in-part of application No. PCT/IL2009/001141, filed on Dec. 3, 2009.

(30) Foreign Application Priority Data

Dec. 4, 2008 (IL) .......................... 195746

(51) Int. Cl.
*A61K 31/70* (2006.01)
*A01N 43/04* (2006.01)

(52) U.S. Cl.
USPC .................. 514/34; 514/27; 514/33

(58) Field of Classification Search
None
See application file for complete search history.

(56) References Cited

U.S. PATENT DOCUMENTS

| 6,667,278 B2 | 12/2003 | Back et al. |
| 2008/0292560 A1 | 11/2008 | Tamarkin et al. |

FOREIGN PATENT DOCUMENTS

| RU | 97 117 958 | | 8/1999 |
| RU | 97 117 959 | | 8/1999 |
| WO | 2009024103 | | 2/2009 |
| WO | WO2009/024103 | * | 2/2009 |

OTHER PUBLICATIONS

Sakakibara et al., Heterocycles, vol. 17, 301-304, 1982.*
WO 2010/064242 A1 with international search report, published Jun. 10, 2010, 12 pages.
Mikolajczyk et al., Urology, 55, pp. 41-44, 2000.
Itami et al., J. Dermatol.Sci., 7, pp. S98-S103, 1994.
Sunhyae et al., J.Steroid Biochem. and Mol.Biol., 107[3-5], pp. 245-252, 2007.
Carraro et al., Prostate, 29, pp. 231-240, 1996.
Wolf et al., MMW Fortschr. Med., 141, pp. 38-40, 1999.
Moore et al., Methods Enzymol., 36, pp. 466-474, 1975.
Yi Jin, Best Practice & Res. Clin. Endocrin. and Metabolism, 15[1], pp. 79-94, 2001.
Neeman et al., Urol. Res., 26, pp. 265-270, 1998.
Washman et al.: Antivir. Chemother. 11 (2000) 71-7.
Malikova J. et al.: Phytochemistry 69(2) (2008) 418-26.
Rosati F. et al.: Endocrinology 144 (2003) 220-9.
Burkhart C.G. and Burkhart C.N. Journal of Drugs in Dermatology, Jul.'Aug. 2004.
Gaines K.K.: Urologic Nursing, Jun. 1, 2003.
Smith C. et al.: J. Clin. Endocrinol. Metab. 81(4) (1996) 1361-6.
Zullo, Braz. J. Plant Physiol., 14(3):143-181, 2002.
Heinlein, CA, Chang C., Endocrine Review. Apr. 2004; 25(2): 276-308.
Khripach, Annals of Botany 86: 441±447, 2000.
IPRP for corresponding PCT application—mailed Jun. 7, 2011—4 pages.

* cited by examiner

*Primary Examiner* — Traviss C McIntosh, III
(74) *Attorney, Agent, or Firm* — Roach Brown McCarthy & Gruber, P.C.; Kevin D. McCarthy

(57) ABSTRACT

Provided are formulations containing brassinosteroids or their derivatives for treating androgen-associated conditions, such as prostate problems. Particularly formulations comprising at least one brassinosteroid or a derivative thereof are provided for treating benign prostatic hyperplasia or androgenic alopecia.

3 Claims, No Drawings

BRASSINOSTEROIDS IN TREATING PROSTATIC HYPERPLASIA AND ANDROGENIC ALOPECIA

FIELD OF THE INVENTION

The present invention relates to formulations comprising brassinosteroids or their derivatives for use in treating androgen-associated conditions, particularly conditions afflicting nearly all men at certain age, such as benign prostatic hyperplasia and androgenic alopecia.

BACKGROUND OF THE INVENTION

Benign prostatic hyperplasia and androgenic alopecia are two androgen-associated conditions that afflict nearly half of middle-aged men, the proportion progressively increasing with age. The former condition, urethra obstruction caused by hypertrophied prostatic gland, may develop into more severe problems without treatment, whereas the latter, male baldness, is rather a cosmetic problem. However, both conditions may cause great inconvenience, and psychological or physical suffering.

Androgenic alopecia (AGA), which may affect also women, is inherited as a polygenic disorder, probably involving multiple pathways, but the precise mechanism remains unknown. Similarly, although benign prostatic hyperplasia (BPH) affects almost all men to some degree as they age, the specific etiology of BPH remains also unknown. AGA shares a number of endocrinologic pathways with BPH. A principal peripheral androgen, dihydrotestosterone (DHT), is formed by converting testosterone in the prostate gland, and blocking the conversion was shown to reduce the size of the prostate gland [Mikolajczyk et al.: Urology 55 (2000) 41-4]. The conversion is catalyzed by a membrane-bound enzyme, 5-α-reductase (5αR), present in the prostate gland and also in susceptible scalp hair follicles [Itami et al.: J. Dermatol. Sci. 7 (1994) S98-103]. DHT is believed to be a major player in androgenetic alopecia [Sunhyae J. et. al.: J. Steroid Biochem. and Mol. Biol. 107(3-5) (2007) 245-52].

The treatments available for AGA have consisted mainly of topically administered minoxidil, and of orally administered finasteride. Finasteride has been also used for treating BPH. However, minoxidil was shown to be scalp flaking and irritating, and eventually can cause itching or skin rash. Finasteride has been implicated with the several adverse reactions, including decreased libido, erectile dysfunction, and ejaculation disorder [Carraro J. C. et al.: Prostate 29 (1996) 231-40]. Further, in females was finasteride contraindicated as a result of its teratogenic potential [Wolf H. et al.: M M W Fortschr. Med 141 (1999) 38-40]. It is therefore an object of this invention to provide an alternative therapeutic means for treating benign prostatic hyperplasia and androgenic alopecia.

It is another object of this invention to provide a therapeutic means for treating androgen-associated conditions selected from benign prostatic hyperplasia and androgenic alopecia, which would be effective and safe, and free of side effects associated with known therapies.

It is still another object of this invention to provide a therapeutic means for treating androgen-associated conditions, which means would be based on plant-derived hormones.

Other objects and advantages of present invention will appear as description proceeds.

SUMMARY OF THE INVENTION

The present invention provides a pharmaceutical formulation for treating an androgen-associated condition selected from benign prostatic hyperplasia and androgenic alopecia comprising at least one brassinosteroid or a derivative thereof comprising at least one brassinosteroid or a derivative thereof of formula I:

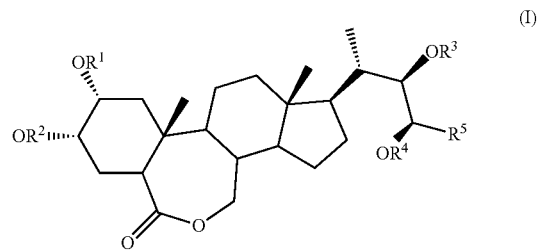

wherein R1, R2, R3, and R4 are independently selected from hydrogen, acyl, alkyl, alkenyl, and glucopyranosyl, and R5 is selected from alkyl and alkenyl.

The pharmaceutical formulation comprises as active ingredient a brassinosteroid, and further comprises a pharmaceutically acceptable carrier, excipient, or diluent. In one embodiment, the pharmaceutical formulation according to the invention comprises an additional active agent selected from antiviral, antibacterial, antifungal, immunomodulator, and antibiotic. Said brassinosteroid derivative may comprise, for example, an ester or ether or glycoside comprising a hydroxyl group of the brassinosteroid molecule.

In one aspect, the invention relates to a method of treating an androgen-associated condition selected from benign prostatic hyperplasia and androgenic alopecia in a subject in need thereof, comprising administering to said subject an effective amount of at least one brassinosteroid or a pharmaceutically acceptable derivative thereof of formula I:

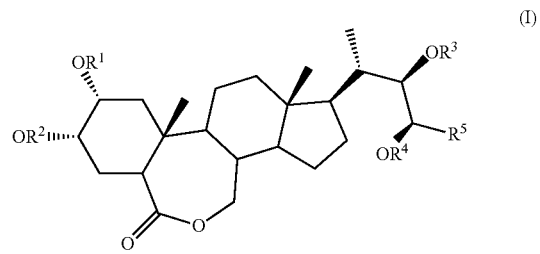

wherein $R^1$, $R^2$, $R^3$, and $R^4$ are independently selected from hydrogen, acyl, alkyl, alkenyl, and glucopyranosyl, and $R^5$ is selected from alkyl and alkenyl, in the preparation of a medicament for treating an androgen-associated condition selected from benign prostatic hyperplasia and androgenic alopecia. Said effective amount will depend on the type of derivative that is employed, on the anamnesis of the treated subject, and on the weight of the patient. Said effective amount may be, for example, between 1 μg and 100 mg, or between 10 μg and 10 mg, per a formulation provided daily to an adult person.

In a preferred embodiment, said $R^1$ and $R^2$ are hydrogen atoms. In another preferred embodiment, said $R^3$ and $R^4$ are hydrogen atoms. Said $R^5$ is preferably a branched alkyl or alkenyl, comprising preferably 5-6 carbon atoms.

DETAILED DESCRIPTION OF THE INVENTION

A new method for treating benign prostatic hyperplasia and androgenic alopecia has now been provided, based on administering a compound of naturally occurring brassinosteroid family, or derivatives and isomers thereof, to a patient suffering from the conditions. Said derivatives may include esters or ethers comprising hydroxyl groups on the brassinosteroid molecule. A preferred method according to the invention comprises administering a formulation containing a plant-derived hormone, such as a compound of brassinosteroid family or a derivative thereof. Such derivative may comprise, for example, a brassinosteroid esterified on one of its hydroxyls by a pharmaceutically acceptable acid. The derivative may comprise a brassinosteroid esterified on more than one of its hydroxyl groups. In other embodiment, the derivative may comprise a brassinosteroid-derived ether, in which an alkyl or alkenyl chain is linked to the oxygen atom of one or more of brassinosteroid's hydroxyl groups. In other embodiment, brassinosteroid is glycosylated on one or more of its hydroxyl groups. A brassinosteroid derivative may be metabolized in the body to provide an active product.

In one embodiment of the invention, a formulation for treating benign prostatic hyperplasia comprises epibrassinolide-24 and an additive, the additive being a component selected from carrier, binding agent, stabilizer, adjuvant, diluent, excipient, surfactant, odorant, or dye. In other embodiment of the invention, a formulation for treating alopecia comprises epibrassinolide-24, and an additive, the additive being a component selected from carrier, binding agent, stabilizer, adjuvant, diluent, excipient, surfactant, odorant, or dye.

A formulation according to the invention may further comprise a second pharmaceutically active agent selected from antiviral, antifungal, antibacterial, antiseptic, anti-inflammatory or immunomodulatory, antineoplastic, and analgesic.

It is believed that brassinosteroid or its derivative, as inhibiting testosterone 5-α-reductase, positively affects relevant tissues, namely prostate gland or scalp hair follicles. Based on the assessment of androgen-associated conditions and of agents affecting them, as well as on the results of the instant inventors, brassinosteroid can be used for affecting androgen-associated conditions, such as prostatic hyperplasia, prostatic cancer, and androgenic alopecia, said affecting comprising treating or preventing; for example, brassinosteroid can potentially be used to prevent prostate cancer. When combined with a second active agent, brassinosteroid provides a formulation exhibiting enhanced effects on other related symptoms, or said formulation has prophylactic effects.

The composition according to the invention, comprising a brassinosteroid as active ingredient, is administered, in a preferred embodiment, orally, for example, as tablets or lozenges or capsules, in suspensions or emulsions, or in solutions, in powders or granules, or in syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically acceptable preparations. The tablets may be uncoated or they may be coated by known techniques to delay disintegration and absorption. A composition comprising a brassinosteroid or its derivative may be employed as a food additive. A low toxicity of brassinosteroids enables to employ safely sufficiently high therapeutic doses. For example, daily oral doses, for an adult subject, may comprise from about 10 µg to about 10 mg brassinosteroid or a derivative thereof.

In a method according to the invention, brassinosteroid or a derivative or isomer thereof, may be administered orally or parenterally. For example, a composition comprising brassinosteroid may be administered intramuscularly, intraperitoneally, or intravenously. In one embodiment, the active formulation may be inserted to the body of a subject in need of the treatment by subcutaneous injection. On other embodiment, a deposit or an implant is inserted into the body, providing a slow release of brassinosteroid or a derivative thereof in the body.

When treating androgenic alopecia, for example, a mixture containing a brassinosteroid or its derivative may be used topically, the mixture being either aqueous-based or oil-based, possibly employing surfactants, wherein said mixture may comprise a solution or emulsion or suspension, and it may be formulated by including components adjusting the consistency of the formulation for convenient application, Additives, such as selected from carrier, binding agent, stabilizer, adjuvant, diluent, excipient, odorant, or dye, and optionally other active agents, are employed, and the mixture is adjusted for applying onto the skin as a cream, ointment, shampoo, or in other forms known in the art. A homogeneous mixture to be topically applied may be in the form of liquid, lotion, pomade, gel, hard paste, or spray, etc.

The mixture may be topically applied, for example on the scalp twice a day. The formulation for topical application onto the scalp may comprise brassinosteroid in a concentration of, for example, 10 µg/dl to 10 mg/dl.

When treating benign prostatic hyperplasia, for example, a mixture containing a brassinosteroid or its derivative may be administered orally or parenterally. For example, the active formulation may be inserted to the body of a subject in need of the treatment by subcutaneous injection. An active composition may be injected into the body near to the prostate tissue. A deposit or an implant may be inserted into the body, providing a slow release of brassinosteroid or a derivative thereof in the body. A daily dose for an adult person would be easily determined by a practicing doctor; it could be, for example between 10 µg and 10 mg.

The invention will be further described and illustrated in the following examples.

EXAMPLES

Experiment Procedures

5α-reductase activity of soluble enzyme was measured by the reduction of testosterone at 37° C. during 40 min in a 3-ml enzyme mixture of human foreskin tissue or *Bos taurus* (Bovine) prostatic tissues, containing NADPH, with and without the test compound in parallel with analytical Ventranal standards for Testosterone and DHT. Tissue preparation and enzyme incubations were performed in accordance with Moore et al. (see below) with modifications. All steps were carried out at 4° C. Prostate or foreskin tissue was dissected and homogenized in ice-cold homogenization phosphate buffer at pH 8.0. The homogenate was centrifuged and the resulting cell free supernatant was stored in aliquots at −80° C. Inhibition of the steroid 5α-reductase was measured by incubating the enzyme and testosterone in the presence of a plant extract or a natural compound. The mixtures were separated by HPLC, analytical Ventranal standards for testosterone and DHT were used; the areas corresponding to the peaks of testosterone and DHT were measured, with the C18 reversed phase Phenomenex column on Jasco PU 2089/Varian HPLC system at a test wavelength of 254 and 291 nm in the order given. The ratio of the peak areas gave quantitative measure of the inhibition [Neeman I. et al.: Urol. Res. 26 (1998) 265-70; Moore R. J, et al.: Methods Enzymol 36 (1975) 466-74; Yi Jin: Best Practice & Research Clinical Endocrinology and Metabolism 15(1) (2001) 79-94, Department of Pharmacology, University of Pennsylvania School of Medicine].

Inhibition of 5αR Activity

The activity of 5α-reductase (EC: 1.3.99.5) was checked in human foreskin tissue and in bovine prostatic tissues. Pure compound and plant extracts were tested for their 5α-reductase inhibition activity, in various experiments. Epibrassinolide-24 from EcoChem has been used, 99% purity.

The effect of one of pure brassinosteroids on human soluble prostate 5α-reductase are summarized in Table 1.

As can be seen in Table 1, the brassinosteroid showed a 5αR inhibitory effect; 74% of the human skin reductase activity was inhibited by brassinosteroid, which was more than when using finasteride in 10 times higher concentration.

TABLE 1

The effect of pure brassinosteroid compound on human genital skin 5αR activity; initial testosterone concentration: 0.34 mM

| Samples | Concentration of 5αR inhibitor | DHT/ testosterone (final) | Activity (% of control) |
|---|---|---|---|
| Control | — | 0.1562 | 100 |
| Epibrassinolide-24 | $10^{-7}$M | 0.0404 | 25.9 |
| Finasteride | $10^{-6}$M | 0.0607 | 32.7 |

The full effects of the tested pure plant-derived compounds in the treatment of AGA are being evaluated in clinical trials.

Pharmaceutical Application

A mixture comprising from 10 μg/dl to 10 mg/dl of Epibrassinolide-24 is prepared, either as a lotion or as an emulsion-based cream, employing known components used in the field of pharmaceutical and cosmetic formulations, including surfactants, carriers, binding agents, stabilizers, diluents, odorants, or dyes, and optionally other active agent, such as antiseptic, antifungal, antibacterial, anti-inflammatory. The mixture is applied on scalp twice a day to treat androgenic alopecia.

Brassinosteroid Toxicity

The acute toxicity data for epibrassinolide-24 were obtained at the Sanitary-Hygienic Institute of Belarus. $LD_{50}$ (orally) in mice (female) is more than 1000 mg/kg; $LD_{50}$ (orally and dermally) in rats (male/female) is more than 2000 mg/kg. Dermal toxicity in rats (male/female) is more than 2000 mg/kg. A formulation comprising 0.025% solution of 24-epibrassinolide, in mice and rats (orally and dermally) has an $LD_{50}$ of more than 5000 mg/kg. Repeated experiments confirmed the value of $LD_{50}$ for epibrassinolide-24 orally in mice and showed a value for the liquid formulation of more than 15000 mg/kg (white rats, orally or intranasally). In concentrations of 0.2%, epibrassinolide-24 did not irritate mucous membranes of rabbits' eyes; this compound, or the above solution, did not irritate the skin. The Ames test for mutagenic activity carried out at the Scientific Research Center of Toxicologic and Hygienic Regulation of Biopreparations of Russia, with or without metabolic activation, was negative (*Salmonella typhimurium* TA 1534, TA 1537, TA 1950, TA 98, TA 100). In micronuclear or chromosome abberation tests (mice CBAB1/6), neither epibrassinolide-24 nor the liquid formulation caused spontaneous mutations. Complex biological testing on *Tetrahymena pyriformis* carried out at the Sanitary-Hygienic Institute of Belarus has confirmed the genetic safety of epibrassinolide-24 and the absence of mutagenic activity over seven generations. In acute, subacute, and chronic experiments, epibrassinolide-24 showed low toxicity and very little cumulative effect. In prolonged experiments, 24-epibrassinolide showed no toxicity but a pronounced adaptogenic effect (increasing adaptive ability of the population). Studies on fish toxicity showed no negative effects, but pronounced stimulative and toxico-protective properties. [Vitvitskaya et al.: Pat. Appl. RU 97,117, 958.; Pat. Appl. RU 97,117,959].

While this invention has been described in terms of some specific examples, many modifications and variations are possible. It is therefore understood that within the scope of the appended claims, the invention may be realized otherwise than as specifically described.

The invention claimed is:

1. A method for treating an androgen-associated condition selected from benign prostatic hyperplasia and androgenic alopecia in a subject in need thereof, comprising administering to said subject a pharmaceutical formulation comprising at least one brassinosteroid of formula I or a pharmaceutically acceptable derivative thereof:

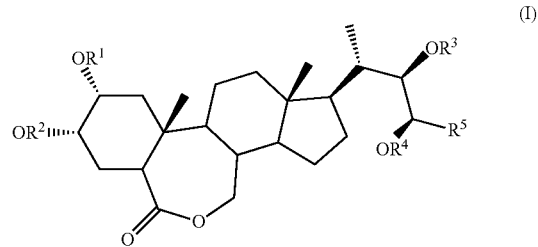

(I)

wherein $R^1$, $R^2$, $R^3$, and $R^4$ are independently selected from hydrogen, acyl, alkyl, alkenyl, and glucopyranosyl, and $R^5$ is selected from alkyl and alkenyl, and wherein said derivative is selected from ester, ether, and glycoside comprising a hydroxyl group of the brassinosteroid molecule.

2. The method according to claim 1, wherein said formulation comprises as active ingredient a brassinosteroid, together with a pharmaceutically acceptable carrier, excipient, or diluent.

3. The method according to claim 1, wherein said formulation comprises an additional active agent selected from antiviral, antibacterial, antifungal, immunomodulator, and antibiotic.

* * * * *